(12) United States Patent
Parsons et al.

(10) Patent No.: US 8,512,725 B2
(45) Date of Patent: Aug. 20, 2013

(54) METHOD, MATERIAL AND SYSTEM FOR CONTROLLED RELEASE OF ANTI-MICROBIAL AGENTS

(75) Inventors: Allen Roland Parsons, Nedlands (AU); Donald William Atkinson, East Victoria Park (AU)

(73) Assignee: Bacstop Corporation Pty Ltd, Welshpool (AU)

( * ) Notice: Subject to any disclaimer, the term of this patent is extended or adjusted under 35 U.S.C. 154(b) by 1082 days.

(21) Appl. No.: 11/662,146

(22) PCT Filed: Sep. 7, 2005

(86) PCT No.: PCT/AU2005/001357
§ 371 (c)(1),
(2), (4) Date: Oct. 8, 2008

(87) PCT Pub. No.: WO2006/026815
PCT Pub. Date: Mar. 16, 2006

(65) Prior Publication Data
US 2009/0104239 A1    Apr. 23, 2009

(30) Foreign Application Priority Data

Sep. 7, 2004   (AU) ............................... 2004905080
Mar. 9, 2005   (AU) ............................... 2005901125

(51) Int. Cl.
*A01N 25/08*   (2006.01)
*A01N 25/12*   (2006.01)
*A01N 25/26*   (2006.01)
*A01N 59/06*   (2006.01)
*A01N 59/20*   (2006.01)

(52) U.S. Cl.
USPC ........... 424/409; 404/405; 404/406; 404/408; 404/411; 404/421; 424/617; 424/618; 424/635; 424/641

(58) Field of Classification Search
None
See application file for complete search history.

(56) References Cited

U.S. PATENT DOCUMENTS

| | | | |
|---|---|---|---|
| 5,211,855 | A | 5/1993 | Antelman |
| 5,223,149 | A | 6/1993 | Antelman |
| 6,346,201 | B1 | 2/2002 | Felkner |
| 6,630,106 | B1 | 10/2003 | Levy |
| 2004/0029834 | A1 | 2/2004 | Schiestel et al. |
| 2004/0103823 | A1 | 6/2004 | Kurihara et al. |

FOREIGN PATENT DOCUMENTS

| | | |
|---|---|---|
| AU | 67658 87 A | 1/1987 |
| AU | 52036 96 A | 7/1996 |
| EP | 0 339 674 | 11/1989 |
| EP | 0 541 231 B1 | 6/1996 |
| EP | 0 566 051 B1 | 7/1996 |
| EP | 1 151 757 A1 | 11/2001 |
| JP | 4 149053 A | 5/1992 |
| JP | 5 123634 A | 5/1993 |
| JP | 6 256052 A | 9/1994 |
| JP | 11 221573 A | 8/1999 |
| WO | WO 98/40465 A1 | 9/1998 |
| WO | WO 03/076341 A2 | 9/2003 |

OTHER PUBLICATIONS

European Search Report for European Patent Application No. 05777674.2, Dec. 22, 2010.

*Primary Examiner* — Neil Levy
(74) *Attorney, Agent, or Firm* — Mintz Levin Cohn Ferris Glovsky and Popeo, P.C.; Ingrid A. Beattie

(57) ABSTRACT

There is provided a method for treating a fluid with an anti-microbial agent comprising the steps of: (a) contacting the fluid with a solid material containing an anti-microbial agent; and, (b) abrading an interface of the solid material and removing particles therefrom and exposing an underlying surface of the solid material to the fluid, thereby facilitating release of the antimicrobial agent of the underlying surface of the solid material and/or the removed particles into the fluid. The solid material comprises an anti-microbial agent dispersed and/or embedded in a solid carrier. Typically, the anti-microbial agent is one or more of a metal, metal oxide, metal compound, metal salt, metal-ligand complex or derivatives thereof based on silver, copper and zinc.

8 Claims, No Drawings

METHOD, MATERIAL AND SYSTEM FOR CONTROLLED RELEASE OF ANTI-MICROBIAL AGENTS

CROSS-REFERENCE TO RELATED APPLICATIONS

This application is the U.S. national phase application of PCT International Application No. PCT/AU2005/001357, filed on Sep. 7, 2005, which claims the benefit of Australian Application Serial No. 2004905080, filed on Sep. 7, 2004 and Australian Application Serial No. 2005901125, filed on Mar. 9, 2005, all of which are hereby incorporated by reference in their entirety.

FIELD OF THE INVENTION

The present invention relates to a method for treating a fluid with an anti-microbial agent. In particular, the present invention relates to a method, material, and system for controllably releasing an anti-microbial agent into a fluid.

BACKGROUND OF THE INVENTION

Several metals and metallic compounds, such as silver, copper and zinc, are well known for their anti-microbial properties. In particular, low concentrations of monovalent silver ions are toxic to micro-organisms. Additionally, silver and silver ions are generally considered to be safe for human consumption at the low concentrations that are effective for anti-microbial applications. Accordingly, the use of metallic silver and silver compounds is particularly advantageous for treating water to obtain water with acceptable levels of microbial organisms for human consumption.

There are several different methods of delivering silver and silver ions into water at low concentrations necessary to observe an anti-microbial effect.

For example, water may be passed through a silver-containing media of activated carbon impregnated with silver salts and metallic silver or an ion exchange medium loaded with monovalent silver ions to increase the concentration of monovalent silver ions in solution to a level which is toxic to micro-organisms. Other silver-containing media, such as high surface area substrates comprising silver or silver compounds have also been used, wherein the method of delivery of solvated silver species is reliant on the slow and continuous dissociation of silver cations into solution at the liquid-solid interface of the substrate.

In all but the purest forms of water, solvated halide ions, particularly chloride ions, are ubiquitous. Thus, it is not surprising that the residence time of monovalent silver ions in solution is typically short and of the order of a few minutes, primarily because of formation of a silver halide precipitate arising from the reaction of monovalent silver ions with solvated halide ions, in particular chloride ions.

$$Ag^+ + Cl^- \rightarrow AgCl(s) \qquad (1)$$

However, the short residence time of monovalent silver ions in solution is considered long enough for an anti-microbial effect to be measurable.

As most water subjected to water treatment will generally contain sufficiently high concentrations of solvated halide ions for silver halide formation to occur, regular replenishment of the water with low concentrations of monovalent silver ions is required to maintain micro-organism populations at acceptable levels for human consumption, particularly if the water is to be stored and not consumed immediately after treatment with silver.

Monovalent silver ions may be rapidly and continuously introduced into aqueous solution by electrolytic means using a silver-containing electrode. However, this method is reliant on an external electrical power source, and it is unsuitable for remote or developing communities where a reliable external power source may be neither available nor affordable.

The effectiveness of all the above described methods is also compromised by the formation of an inert film or coating of silver halide over the liquid-solid interface of the silver-containing media or the silver-containing electrode, which prevents further release of silver into solution.

Similarly, other metals and metal compounds which display anti-microbial properties, such as copper and zinc, are prone to oxidation and the resultant formation of an inert film or coating of metal oxide over the liquid-solid interface of a substrate containing the metals and/or metal compounds.

The efficacy of other forms of silver, such as trivalent silver ions, as anti-microbial agents has also attracted recent attention. In U.S. Pat. No. 5,223,149 Antelman describes treating utilitarian bodies of water, such as swimming pools, hot tubs, municipal and industrial water supplies with a liquid concentrate of soluble Ag(III) complexes, in particular silver(III) periodate and silver(III) biguanide complexes.

Treatment of water by introduction of mixed valency silver compounds has also been examined, although it appears necessary to combine such compounds with an oxidising agent such as persulfate or ozone to afford the required anti-microbial effect. For example, in U.S. Pat. No. 5,211,855 Antelman describes a method of treating utilitarian bodies of water with tetrasilver tetroxide molecular crystals in the presence of oxidizing agents such as persulfate, whereas in U.S. Pat. No. 6,346,201 Felkner describes a water disinfection method employing ozonated tetrasilver tetroxide and compositions comprising ozonated tetrasilver tetroxide.

It will be appreciated that there is thus a need to provide a means of controllably releasing an antimicrobial agent or other active substance into a fluid without the direct need for electric power.

In the art of garment bleaching, European patent publication EP0339674 discloses an attrition method for releasing bleaching agent from a solid carrier to a second solid material, namely a garment to be bleached. Here, attrition between garment and the solid carrier transfers particles of an oxidising agent contained in a cement matrix to moisture present in the garment against which it is abraded. The particles are not released into a fluid that is free-flowing. Furthermore, the attrition method is difficult to control and does not readily enable a controlled release of bleaching agent.

The present invention seeks to overcome at least in part some of the aforementioned disadvantages.

It is to be understood that, although prior art use and publications are referred to herein, such reference does not constitute an admission that any of these form a part of the common general knowledge in the art, in Australia or any other country.

SUMMARY OF THE INVENTION

The prior art has demonstrated that a continuous release of a metal or a metal compound displaying anti-microbial properties from a substrate or an electrode is sometimes compromised by formation of an inert film or coating, typically a metal halide or a metal oxide, over the liquid-solid interface of the substrate or electrode, thus preventing further release of the metal or metal compound into the fluid.

The present invention is based on the realisation that it is possible to controllably release low concentrations of such metals or metal compounds into the fluid by abrading a liquid-solid interface of a substrate containing the metal or metal compound to remove the inert film or coating.

Thus, according to one feature of the invention there is provided a method of controllably releasing an anti-microbial agent into a fluid comprising the steps of:
 a) contacting the fluid with a solid material containing the anti-microbial agent; and, b) abrading an interface of the solid material and removing particles therefrom and exposing an underlying surface of the solid material to the fluid, thereby facilitating release of the anti-microbial agent at the underlying surface of the solid material and/or the removed particles into the fluid.

The term "anti-microbial agent" as used herein refers to a substance which acts to reduce a total number of viable micro-organisms including but not limited to bacteria, fungi, and viruses. In some embodiments of the invention the anti-microbial agent is an anti-bacterial agent. In some embodiments of the invention the anti-microbial agent is an anti-fungal agent. In some embodiments of the invention the anti-microbial agent is an anti-viral agent.

Typical examples of microorganisms which can be inhibited by the anti-microbial agent of the present invention include, but are not limited to, *Escherichia coli, Pseudomonas aeruginosa, Bacillus cereus*, coliform bacteria, and thermotolerant coliform bacteria.

The anti-microbial agent can be any one or more of a metal, metal oxide, metal compound, metal salt, metal-ligand complex or derivatives thereof having anti-microbial properties. Typical examples of the anti-microbial agent comprise, but are not limited to, any one or more of a metal, metal oxide, metal compound, metal salt, metal-ligand complex or derivatives thereof based on silver, copper, and zinc.

In the preferred embodiment, the anti-microbial agent is silver oxide (AgO), also sometimes referred to as tetrasilver tetroxide. While not wishing to be bound by theory, the inventors opine that when silver oxide is exposed at the underlying surface of a particle removed from the abraded material or at the underlying surface of the abraded solid material, silver oxide rapidly reacts in aqueous solution to afford solvated silver ions. The solvated silver ions have a residence time in solution sufficiently long for an anti-microbial effect to be measurable.

The fluid can be a gas or a liquid. A water-based liquid is the preferred fluid. Typical examples of water-based liquids comprise, but are not limited to, beverages (eg. bottled water, municipal drinking water supplies, fruit and/or vegetable juices, still and carbonated beverages), biological fluids or water-based fluids used in therapeutic or pharmaceutical applications (eg. serum, saline solutions, dental unit water supplies), water used for human and/or animal consumption (eg. municipal water supplies), water used in recreational activities (eg. swimming pools), water used in manufacturing and industrial applications (eg. as a raw material, solvent, process stream, in cooling towers, air conditioning systems, cleaning fluids), and water used in aquaculture.

In some embodiments, the fluid can be a gas in the form of steam, humidified air, or air-borne water in the form of an atomised or nebulised spray. In other embodiments, the fluid can be gases used in breathing apparatus, gases used in medical and surgical applications, gases used under sterile conditions in industrial applications.

The term "interface" as used herein refers to a surface forming a common boundary between a solid phase, in particular the solid material, and the fluid in contact with the solid phase.

In one embodiment, the step of abrading the interface of the solid material comprises providing a plurality of solid bodies of the solid material and agitating the fluid or otherwise causing the solid bodies to collide on a controlled basis and thereby partially fragment the solid bodies and release the anti-microbial agent into the fluid.

In one embodiment, the step of agitating the fluid comprises stirring the fluid at a rate which causes the solid bodies to collide.

In an alternative embodiment, the step of agitating the fluid comprises shaking the fluid at a rate which causes the solid bodies to collide.

In a further embodiment, the step of agitating the fluid comprises containing the fluid and the solid bodies in a vessel, and recirculating the fluid through the vessel, the arrangement being such that the flux of fluid into or out of the vessel causes the solid bodies to collide.

In an alternative embodiment, the step of abrading an interface of the solid material comprises applying an abrasive force directly on the interface of the solid material. Typically, the abrasive force is directly applied on the interface of the solid material by an abrading means, such as for example, a mechanical scourer.

According to a second feature of the invention there is provided a solid material for controllably releasing an anti-microbial agent into a fluid, the solid material comprising an anti-microbial agent dispersed or embedded in a solid carrier.

Typically the solid carrier is selected to provide the solid material with desirable hardness, strength, porosity and particle size properties. Additionally, it is desirable that the solid carrier is not appreciably soluble in water so that the solid material maintains its bulk structural integrity while in contact with water-based fluids.

In some embodiments the solid carrier is a cementitious material. The term "cementitious material" as used herein refers to a substance used for bonding or setting to a hard material. Typical cementitious materials include, but are not limited to hydraulic cements such as for example, Portland cement, Portland-slag cement, Portland-pozzolan cement, slag cement, natural cement, masonry cement, or sulphate-resistant cement, or organic cementitious materials such as epoxy resins and polyester resins.

In other embodiments the solid carrier is a bulking agent provided with desirable hardness, strength, porosity, particle size, and solubility properties.

Optionally, the solid material further comprises an adjunct selected from the group consisting of a flocculant, a coagulant, an inert particulate material, a buoyancy agent, a further hardening agent, a water treatment agent, a nutrient and/or a therapeutic agent.

In a third feature of the invention there is provided a device coated in a solid material for controllably releasing an anti-microbial agent into a fluid, wherein the solid material comprises an anti-microbial agent dispersed or embedded in a solid carrier.

In a fourth feature of the invention there is provided a system for controllably releasing an anti-microbial agent into a fluid, the system comprising:

a receptacle for receiving the fluid;

a solid material containing an anti-microbial agent, wherein an interface of the solid material is disposed in the receptacle and is in contact with the fluid received in the receptacle; and a means for abrading the interface of the solid material and removing particles therefrom and exposing an underlying surface of the solid material to the fluid, thereby facilitating release of the anti-microbial agent at the underlying surface of the solid material and/or the removed particles into the fluid.

In a fifth feature of the invention there is provided a method of controllably releasing an anti-microbial agent into a fluid, comprising the steps of:

dispersing and/or embedding an anti-microbial agent in a material;

forming a solid body of the material containing the dispersed and/or embedded anti-microbial agent;

locating a plurality of the solid bodies in a chamber containing the fluid to be treated; and, agitating the fluid or otherwise causing the solid bodies to collide on a controlled basis and thereby partially fragment the solid bodies and release the anti-microbial agent into the fluid.

In another feature of the invention there is provided a method of treating a fluid with an anti-microbial agent comprising the steps of:

a) contacting the fluid with a solid material containing the anti-microbial agent; and, b) abrading an interface of the solid material and removing particles therefrom and exposing an underlying surface of the solid material to the fluid, thereby facilitating release of the anti-microbial agent at the underlying surface of the solid material and/or the removed particles into the fluid.

In the description of the invention and the claims defining the invention, except where the context requires otherwise due to express language or necessary implication, the words "comprise" or variations such as "comprises" or "comprising" are used in an inclusive sense, i.e. to specify the presence of the stated features, but not to preclude the presence or addition of further features in various embodiments of the invention.

DETAILED DESCRIPTION OF THE PREFERRED EMBODIMENTS OF THE INVENTION

Before the preferred embodiment of the present apparatus is described, it is understood that this invention is not limited to the particular materials described, as these may vary. It is also to be understood that the terminology used herein is for the purpose of describing the particular embodiment only, and is not intended to limit the scope of the present invention in any way. It must be noted that as used herein, the singular forms "a", "an", and "the" include plural reference unless the context clearly dictates otherwise. Unless defined otherwise, all technical and scientific terms used herein have the same meanings as commonly understood by one of ordinary skill in the art to which this invention belongs.

The inventors have found that an anti-microbial agent can be controllably released into a fluid by contacting the fluid with the solid material containing the anti-microbial agent and abrading the interface of the solid material to remove particles therefrom. In this way, an inert film or coating of a metal halide or other metal species formed on the interfacial surface by reaction of the anti-microbial agent with other ubiquitous chemical species in the fluid will be removed. Upon removal of the particles, an underlying surface of the solid material is exposed to the fluid, whereupon the anti-microbial agent at the underlying surface of the solid material and/or the removed particles is released into the fluid.

The inventors have developed a solid material to facilitate the methods of the present invention, wherein the solid material comprises an anti-microbial agent dispersed or embedded in a solid carrier.

The anti-microbial agent can be one or more of a metal, metal oxide, metal compound, metal salt, metal-ligand complex or derivatives thereof having anti-microbial properties. Typical examples of an anti-microbial agent include but are not limited to a metal, metal oxide, metal compound, metal salt, metal-ligand complex or derivatives thereof known to have anti-microbial properties based on silver, copper, and zinc.

Preferably, the anti-microbial agent is silver oxide, copper (II) oxide, and zinc (II) oxide. Silver oxide is stoichiometrically represented as AgO but neutron diffraction has shown that it is $Ag^I Ag^{III} O_2$ with two types of silver atom in the lattice, one with linear coordination to two oxygen atoms ($Ag^I$) and the other with square planar coordination with respect to oxygen ($Ag^{III}$). It is a powerful oxidizing agent and has been selected as an anti-microbial agent because it demonstrates desirable properties, such as low bulk solubility, resistance to photolytic degradation, and good storage stability over prolonged periods.

Typically, the solid carrier is selected to provide the solid material with desirable hardness, strength, porosity and particle size properties. Additionally, it is desirable that the solid carrier is not appreciably soluble in the fluid so that the solid material maintains its bulk structural integrity while in contact with the fluid.

In some embodiments the solid carrier is a cementitious material. Typical cementitious materials include, but are not limited to hydraulic cements such as for example, Portland cement, Portland-slag cement, Portland-pozzolan cement, slag cement, natural cement, masonry cement, or sulphate-resistant cement, or organic cementitious materials such as epoxy resins and polyester resins. In particular, sulphate-resistant cement demonstrates desirable slow-curing properties and stability in conditions where populations of sulphur-reducing bacteria are active and sulphate anions are produced.

In other embodiments the solid carrier is a bulking agent provided with desirable hardness, strength, porosity, particle size, and solubility properties.

Typically, the solid carrier also serves to dilute the proportion of the anti-microbial agent in the solid material such that the solid material may be manufactured at relatively low cost while at the same time having sufficient anti-microbial agent present in the solid material to controllably release a desirable concentration of the anti-microbial agent into the fluid.

Upon employing the method of the present invention particles of the solid material are removed and enter the fluid. The size and concentration of the removed particles entering the fluid will necessarily vary according to many factors, including the hardness of the solid material and the abrasion forces applied to the solid material. It is thus an important consideration to select a solid carrier that is non-toxic at the concentrations at which the removed particles will be present in the fluid if the purpose of the fluid is for human or animal consumption.

Portland cement is one of the preferred solid carriers as it is inexpensive and readily available, structurally stable over prolonged periods, inert and non-toxic at concentrations at which it would be likely to be consumed. For instance, many existing water storage reservoirs and water conduits are already constructed from the solid carrier(s) envisaged for use in this invention.

In an alternative embodiment the solid carrier can be the anti-microbial agent. For example, a solid material of silver oxide (AgO) can be formed by compacting an amount of dried silver oxide (AgO) powder in an appropriately shaped die at pressures in the order of 20 bar.

Optionally, the solid material further comprises an adjunct comprising any one or more of components selected from a group comprising a coagulant, a flocculant, a water treatment agent, an inert particulate material, a buoyancy agent, a hardening agent, a nutrient and/or a therapeutic agent.

A coagulant is an agent causing extremely fine colloidal particles to adhere directly to each other, while a flocculant is an agent causing the aggregation of particles in colloidal form into larger masses to aid separation thereof by filtration and other known solid separation means. Controlled release of one or both of the coagulant and/or the flocculant together with the anti-microbial agent in water-based fluids can be afforded in accordance with the methods herein described. It is thought that addition of the coagulant and/or the flocculant to the water-based fluids, such as municipal drinking water supplies for example, will augment general water treatment processes to produce potable water. Several coagulants, flocculants and water treatment agents are known to the person skilled in the art of water treatment which are suitable for this application.

In certain applications and operating conditions it may also be desirable to provide an solid material further comprising an inert particulate, a buoyancy agent such as phenolic resin microballoons, silica microballoons, and polystyrene beads, and/or a further hardening agent.

It may also be desirable to provide the solid material with an odourant or a colourant dispersed throughout the solid material to readily indicate if and when the anti-microbial agent is present in the treated water.

A nutrient and/or a therapeutic agent may be advantageously combined with the anti-microbial agent in the solid material, whereby, in use, abrasion of the solid material in accordance with the present invention will also controllably release a nutrient and/or a therapeutic agent together with the anti-microbial agents into the fluid. For example, in remote communities where iodine deficiencies are prevalent, the solid material may be prepared such that it also includes bioavailable iodine. Subsequent abrasion of the solid material in drinking water supplies will concurrently controllably release bioavailable iodine into the drinking water supplies, which can then be consumed with beneficial nutritional effects to the recipient. Antibiotics, hormones, vitamins, and other nutrients or therapeutic agents may also be advantageously stored in the solid material and then controllably released at low concentrations into water-based fluids together with the anti-microbial agent in accordance with the methods hereinbefore described.

The solid material is prepared by mixing the anti-microbial agent and the solid carrier in a ratio of between 95:5-1:99 wt %. Typically, the anti-microbial agent and the solid carrier are present in the solid material in a ratio of between 50:50-85:15 wt %. Depending on the nature of the solid carrier an appropriate curing agent, such as water, and optionally the adjunct as previously described may be added to the mixture. The resulting wet mixture may be formed into solid bodies such as pellets, spheroids, ellipsoids or other desired shapes, before undergoing curing and hardening processes.

Alternatively, the resulting wet mixture can be coated onto a device such as pellets, spheroids, ellipsoids or other desired shapes, before undergoing final curing and hardening processes. A coating of the solid material can be advantageously applied to interior surfaces (or portions thereof) of a vessel for fluid storage, a receptacle for receiving fluids, or a conduit through which fluids pass.

The coating of the solid material can also be applied to a core of material comprising an odourant, a colourant, or an indicator agent, to indicate the end-life of the coating and prompt replacement of the solid material when the solid material is abraded to an extent whereby the core of material is exposed.

The term "coating" or "coated" as used herein refers to a layer of solid material applied to a solid surface. It will be understood that the layer of solid material applied to the solid surface can extend over one or more portions of the solid surface or the entire extent of the solid surface.

Typically, the size of a solid body formed from, or coated with the solid material of the present invention can range from 10 microns-100 mm.

Devices coated with the solid material of the present invention can exhibit extensive surface areas coated with the solid material at thicknesses of 10 microns-100 mm. For example, an interior surface of a fluid storage vessel can be provided with a 1 mm coating of the solid material.

The inventors have provided a method of controllably releasing an anti-microbial agent into a fluid comprising the steps of:
  a) contacting the fluid with a solid material containing the anti-microbial agent; and,
  b) abrading an interface of the solid material and removing particles therefrom and exposing an underlying surface of the solid material to the fluid, thereby facilitating release of the anti-microbial agent at the underlying surface of the solid material and/or the removed particles into the fluid.

In one embodiment of the invention at least two pellets formed from, or coated with, the solid material are located in a vessel for treating and/or storing fluid. The vessel is provided with an agitation means. The pellets are then agitated by the agitation means whereby the pellets are caused to tumble against each other, thus effecting abrasion at the interface of the pellets so that small particles are removed therefrom.

Typically, the small particles comprise a portion of an insoluble film, for example a silver halide film, which forms over time over the interface of the pellets and/or a portion of the solid material. Once the portion of the insoluble film has been removed, the underlying surface of the solid material and/or the underlying surface of the portion of the removed solid material particle are exposed to contact with the fluid. The anti-microbial agent at the underlying surface of the solid material and/or the removed particles then reacts with the fluid to release the anti-microbial agent into the fluid.

If the solid material contains additional components comprising the adjunct, such as a flocculant and/or a coagulant, a water treatment agent, a nutrient and/or a therapeutic agent, then it will be understood that the additional components exposed at the underlying surface of the solid material and/or the underlying surface of the portion of the solid material removed from the abraded interfacial surface will also be exposed to contact with the fluid. In this way, the additional components comprising the adjunct may also be controllably released into the fluid.

The agitation means is typically mechanical, such as a rotating impeller or stirrer, and located in the vessel to agitate the pellets and/or the fluid contained in the vessel to a degree whereby the pellets are caused to tumble against one another, thus effecting abrasion at the interface of the pellets and removing small particles therefrom.

Alternatively, the agitation means is located externally of the vessel and is adapted in use to agitate the vessel and its contents such that the contents of the vessel are shaken or disturbed and the pellets are caused to tumble against one another, thus abrading the interface of the pellets and removing small particles therefrom.

Alternatively, the agitation means is a hydraulic agitation means, wherein the vessel is provided with a means to recirculate fluid, either gas or liquid, through the contents of the vessel, the arrangement being such that the flux of fluid into or out of the vessel hydraulically agitates the pellets so that they are caused to tumble against one another, thus abrading the interfacial surface of the pellets and removing small particles therefrom. Typically, the flux of fluid into or out of the vessel is 10-30 litres/minute.

In another embodiment of the invention, a vessel can be provided with a coating of the solid material on at least a portion of its interior surface. The vessel is provided with at least one freely moving element that is adapted, in use, to abrade the solid material coated on the interior surface of the vessel. Typically, the or each freely moving element is formed from, or coated with, the solid material. Alternatively, the or each freely moving element is formed from, or coated with, a material whose hardness is sufficient to effect abrasion of the solid material on the interior surface of the vessel. The vessel is provided with any one of the agitation means previously described. The or each freely moving element is then agitated by the agitation means whereby it tumbles against the solid material coated on the portion of the interior surface of the vessel, thus abrading the interface of the solid material and removing small particles therefrom.

Abrasion of the solid material on the interior surface of the vessel can be facilitated by abrasive forces acting directly on the solid material exerted by an external abrading means, such as a mechanical scourer.

Advantageously, the rate of abrasion of the interface of the solid material can be selected to control release of the anti-microbial agent. For example, continuous abrasion of the solid material might, in some cases, introduce an excessively high concentration of anti-microbial agent into the fluid. The concentration of anti-microbial agent released into the fluid may be decreased by reducing the rate of abrasion, or even by ceasing abrasion for pre-determined periods.

In some embodiments the anti-microbial agent is capable of forming an inert film or coating by reacting with one or chemical species contained in the fluid. In these instances, reducing the rate of abrasion or even ceasing abrasion for pre-determined periods will encourage partial or full formation of the inert coating of the metal halide or metal oxide or other metal species formed on the interface of the solid material thereby limiting dissolution of the anti-microbial agent at the interface of the solid material until the inert coating is further abraded.

For example, and as described previously, a silver halide film will inevitably form on any interfacial surface containing silver in the presence of solvated halide ions. Whilst abrasion of the interfacial surface will remove the silver halide film, cessation of the abrasive action on the interfacial surface will result in the re-formation of the silver halide film over a period of time, thereby preventing further dissolution of the anti-microbial agent contained in the abrasive material. The method of the present invention therefore harnesses the ability to remove the silver halide film or re-form the silver halide film to control the rate of release of the silver-based anti-microbial agent into the surrounding fluid.

The rate of abrasion of the interface of the solid material can be controlled so that the concentration of anti-microbial agent released into the fluid is sufficient to afford an anti-microbial effect.

The concentration of the anti-microbial agent released into the fluid in accordance with the methods of the present invention will also be determined by any one of or a combination of several factors including, but not limited to, the concentration of the anti-microbial agent in the solid material, the surface area of the particle removed from the interface of the solid material and the surface area of the underlying surface of the solid material exposed, and the number of particles removed from the interface of the solid material within a given period of time. These factors, to some extent, will be directly or indirectly dependent on the hardness of the solid material and the abrasive force applied to the solid material.

The abrasive force applied to the solid material will be determined by any one of or a combination of several factors including, but not limited to, the hardness of the solid material with which the solid bodies are formed or coated, the hardness of the freely moving elements caused to tumble in the vessel, size of the solid bodies and/or freely moving elements, weight of the solid bodies and/or freely moving elements, the rate of collisions, volume of the vessel, and rate of flux of the fluid into and out of the vessel.

The invention will now be further described with reference to the following examples.

Example 1

Dry silver oxide (AgO) powder (75 g) was intimately mixed with dry Portland cement (25 g) and deionized water (20 ml) to form a mixture with a paste-like consistency. Small portions (5 g) of the mixture were worked in an orbital fashion against another surface to form spheroids approximately 12-15 mm in diameter. The spheroids were allowed to harden for several hours and were allowed to cure under water to achieve full strength.

Spheroids can also be formed in a similar manner as described above based on a dry mixture of silver oxide (AgO) powder (60 g), general purpose cement (36 g), and Corrocem™ (4 g).

Example 2

Several spheroids prepared in accordance with Example 1 were immersed in water contained in a cylindrical vessel with a conical base. The conical base was provided with a central aperture in fluid communication with a means for recirculating water through the cylindrical vessel, the arrangement of the aperture and said means being such that the flow of recirculated water into the vessel caused the spheroids to tumble against one another.

Aliquots of the recirculated water were sampled at intervals of 5, 10, 20, and 40 minutes. The concentration of silver in each of the aliquots was determined by atomic absorption spectroscopy (AAS) as 50 ppb, 111 ppb, 190 ppb, and 373 ppb, respectively.

Several bacterial organisms, *E. coli* ATCC 11775, *Pseudomonas aeruginosa* ATCC 27853, and *Bacillus cereus* NCTC 10320 were inoculated into equal volumes of the abovementioned aliquots to achieve an initial bacterial concentration of approximately $10^6$ cells per millilitre. After three predetermined time periods of 5 minutes, 1 hour, and 8 days, aliquots of each solution were withdrawn, and enumeration of surviving organisms was performed. All tests were conducted in duplicate.

Control solutions were run in parallel with the test solutions as follows:
1) Blank controls comprised sterile, untreated water inoculated with the abovementioned bacterial organisms.
2) Chlorine controls comprised sterile water treated with sodium hypochlorite (0.5 ppm), at levels comparable to standard drinking water, inoculated with the abovementioned bacterial organisms.

The results of the tests are summarized in the following Tables. All results are expressed in $\log_{10}$ units.

TABLE 1

E. coli. (Initial concentration of organism in solution is 5.81)

| Period | Silver concentration | | | | Controls | |
|---|---|---|---|---|---|---|
| | 50 ppb | 111 ppb | 190 ppb | 373 ppb | Blank | NaOCl |
| 5 min | 5.81 | 5.77 | 5.76 | 5.79 | 5.82 | 5.82 |
| 1 hour | 4.79 | 4.48 | 3.74 | 3.88 | 5.69 | 5.81 |
| 8 days | 0 | 0 | 0 | 0 | 0 | 4.48 |

TABLE 2

Pseudomonas aeruginosa. (Initial concentration of organism in solution is 5.62)

| Period | Silver concentration | | | | Controls | |
|---|---|---|---|---|---|---|
| | 50 ppb | 111 ppb | 190 ppb | 373 ppb | Blank | NaOCl |
| 5 min | 5.61 | 5.61 | 5.61 | 5.62 | 5.61 | 5.62 |
| 1 hour | 5.27 | 4.98 | 5.00 | 5.10 | 5.62 | 5.63 |
| 8 days | 3.23 | 2.59 | 1.10 | 2.00 | 4.33 | 4.98 |

TABLE 3

Bacillus cerus. (Initial concentration of organism in solution is 5.82)

| Period | Silver concentration | | | | Controls | |
|---|---|---|---|---|---|---|
| | 50 ppb | 111 ppb | 190 ppb | 373 ppb | Blank | NaOCl |
| 5 min | 4.60 | 4.20 | 4.28 | 4.19 | 4.90 | 4.61 |
| 1 hour | 2.30 | 2.00 | 1.93 | 0 | 4.88 | 4.61 |
| 8 days | 0 | 0 | 0 | 0 | 5.26 | 4.90 |

Example 3

Several spheroids prepared in accordance with Example 1 were installed in a receptacle together with a post-filtration device in a water recirculation loop coupled to an operational cooling tower. Water from a small take-off located on the recirculation pump discharge pipe and returned to the cooling tower sump via a hose was treated in accordance with the invention. Water recirculated continuously past the spheroids, the flow of the recirculating water causing the spheroids to tumble against one another, while the cooling tower was in operation. The small take-off permitted a relatively small volume of water to be treated per minute so that the recirculation rate of the entire volume of the cooling tower water through the receptacle was relatively low.

Water samples were collected in a sterilized glass bottle from the hose that returned water to the cooling tower, and removed promptly to the laboratory for microbial analyses according to the following tests:

| Test Part 1 | |
|---|---|
| Heterotrophic Plate Count | Method |
| at 21° C. CFU per mL | MMM 4.1W |
| at 37° C. CFU per mL | MMM 4.1W |

Samples were collected before treatment commenced, one week after treatment commenced and two weeks after treatment commenced. After two weeks of treatment, the spheroids were removed from the recirculation loop and water samples were collected after one week had elapsed from cease of treatment and after two weeks had elapsed from cease of treatment.

Heterotrophic Plate Count (HPC) is used as an indicator for general water quality. The test requires bacterial incubation at temperatures of 21° C. and 37° C. for a set time. Populations of <100,000 Colony forming units (CFU) per mL are generally acceptable in cooling towers. Populations greater than this usually require remedial action.

TABLE 4

Results of Test Part 1

| | Date | | | | |
|---|---|---|---|---|---|
| | 9 Sep. 2004 | 17 Sep. 2004 | 24 Sep. 2004 | 1 Oct. 2004 | 12 Oct. 2004 |
| | Lab Number | | | | |
| | 0423651W | 0424486W | 0425166W | 0425860W | 0426588W |
| | Sample Condition | | | | |
| Heterotrophic Plate Count | Untreated | Treated | Treated | Untreated | Untreated |
| at 21° C. CFU per mL | 2,000 | 22,000 | 2,700 | 70,000 | 300,000 |
| at 37° C. CFU per mL | 86,000 | 38,000 | 4,200 | 72,000 | 47,000 |

Example 4

Several spheroids prepared in accordance with Example 1 were installed in a receptacle together with a post-filtration device and attached to an electric pump mounted onto the laboratory bench. Cooling tower water was continuously recirculated through the receptacle. A sample was taken prior to starting the recirculation pump. Samples were collected after 5, 10, 15 and 30 minutes of recirculation. The recirculation rate was 15 L/min.

Samples were removed promptly to the laboratory for microbial analyses according to the following tests:

| Test Part 2 Heterotrophic Plate Count | Method |
|---|---|
| at 21° C. CFU per mL | MMM 4.1W |
| at 37° C. CFU per mL | MMM 4.1W |

TABLE 5

Results of Test Part 2

| | Date 27 Oct. 2004 Treatment Duration | | | |
|---|---|---|---|---|
| | 0 minutes | 5 minutes | 15 minutes | 30 minutes |
| | | Lab Number | | |
| | 0428127W | 0428128W | 0428130W | 0428131W |
| | | Sample Condition | | |
| Heterotrophic Plate Count | Untreated | Treated | Treated | Treated |
| at 21° C. CFU per mL | 210,000 | 110 | 60 | 0 |
| at 37° C. CFU per mL | 260,000 | 110 | 60 | 20 |

The results of Test Part 1 indicate that reduced colonies of Heterotrophic Bacteria can be maintained at an acceptable level by treating a low effective flow rate of cooling tower water in accordance with the method of the present invention The results of Test Part 2 indicate that in respect of high flow rates of treated cooling tower water, elevated colonies of Heterotrophic bacteria can be rapidly reduced within 5 minutes of exposure to silver anti-microbial agents produced in accordance with the method of the present invention and virtually eliminate the same within 30 minutes of exposure.

Example 5

A 20 L representative water sample was collected from a suburban lake. The sample site was on the water surface, 2-3 metres from the shore in water depths greater than 50 cm. Agitated sedimentation and non representative occurrences were avoided during sample collection.

Four individual 500 mL aliquots were sampled and stored in laboratory grade sterilized glass bottles.

Samples containing the following concentrations of silver, copper, and zinc anti-microbial agents were introduced to the water samples in the manner described below:

| | mg/L | | |
|---|---|---|---|
| Sample Number | AgO | CuO | ZnO |
| 0420333W | Nil | Nil | Nil |
| 0420334W | 0.05 | 0.50 | 0.50 |
| 0420335W | 0.10 | 1.00 | 1.00 |
| 0420336W | 0.15 | 1.50 | 1.50 |

Silver

Two spheroids comprising silver oxide as the anti-microbial agent were enclosed in a 1 µM filter bag attached to a suitable length handle into sample 0420334W. The balls were vigorously shaken by means of the handle for a predetermined period. Subsequent aliquots were sampled and tested with an AAS to measure the silver concentration from time to time until 0.05 mg/L silver concentration in the sample was obtained. A similar procedure was repeated to achieve progressively increase silver concentrations in subsequent water samples:

0420335W to achieve 0.10 mg/L silver in the sample
0420336W to achieve 0.15 mg/L silver in the sample Copper Two spheroids comprising copper oxide as the anti-microbial agent were enclosed in a 1 µM filter bag attached to a suitable length handle into sample 0420334W. The balls were vigorously shaken by means of the handle for a predetermined period. Subsequent aliquots were sampled and tested with an AAS to measure the copper concentration from time to time until 0.50 mg/L copper concentration in the sample was obtained. A similar procedure was repeated to achieve progressively increase copper concentrations in subsequent water samples:

0420335W to achieve 1.00 mg/L copper in the sample
0420336W to achieve 1.50 mg/L copper in the sample Zinc Two spheroids comprising zinc oxide as the anti-microbial agent were enclosed in a 1 µM filter bag attached to a suitable length handle into sample 0420334W. The balls were vigorously shaken by means of the handle for a predetermined period. Subsequent aliquots were sampled and tested with an AAS to measure the zinc concentration from time to time until 0.50 mg/L zinc concentration in the sample was obtained. A similar procedure was repeated to achieve progressively increase zinc concentrations in subsequent water samples:

0420335W to achieve 1.00 mg/L zinc in the sample
0420336W to achieve 1.50 mg/L zinc in the sample Samples were promptly removed for microbial analyses in accordance with the following test:

| Test | Method |
|---|---|
| Hetrotrophic Plate Count | |
| at 21° C. CFU per mL | MMM 4.1W |
| at 37° C. CFU per mL | MMM 4.1W |
| Coliforms | |
| CFU per 100 mL | MMM 4.2W |

TABLE 6

Test Results

| | Untreated | Treated | | |
|---|---|---|---|---|
| Sample Number | 0420333W | 0420334W | 0420335W | 0420336W |
| Hetrotrophic Plate Count | | | | |
| at 21° C. CFU per mL | 3500 | 110 | 100 | 30 |
| at 37° C. CFU per mL | 1100 | 90 | 360 | 70 |
| Coliforms | | | | |
| CFU per 100 mL | 100 | 0 | 0 | 0 |
| Thermotolerant Coliforms | | | | |
| CFU per 100 mL | 37 | 0 | 0 | 0 |

Heterotrophic Plate Count (HPC) is used as an indicator for general water quality. The test requires bacterial incubation at temperatures of 21° C. and 37° C. for a set time. Populations of <500 CFU per mL are generally acceptable, whereas populations >500 CFU per mL usually requires remedial action. The name "Coliform" is given to a whole group of bacteria which can occur in water and indicate potential health problems. They are divided into two groups: coliform, which are all of the coliform bacteria, and thermotolerant (Fecal) coliforms, which are a subset of the group. Both of these bacteria are closely related. The thermotolerant coliform group is considered much more serious from the hygiene viewpoint. In testing, the water counts are normally given in numbers of cells in a 100 mL of sample water. The presence of coliforms in water, and in particular thermotolerant coliform usually leads to serious problems for consumers. CFU means Colony Forming Units.

An anti-microbial effect was observed in all the water samples treated as described above.

Example 6

Several spheroids prepared in accordance with Example 1 were installed in a receptacle together with a post-filtration device and attached to an electric pump mounted onto the laboratory bench. Swimming pool water was continuously recirculated through the receptacle. A sample was taken prior to starting the recirculation pump. Samples were collected after 10, 15 and 30 minutes of recirculation. The recirculation rate was 15 L/min.

Samples were removed promptly to the laboratory for microbial analyses according to the following tests:

| Test | Method |
|---|---|
| Heterotrophic Plate Count | |
| at 21° C. CFU per mL | MMM 4.1W |
| at 37° C. CFU per mL | MMM 4.1W |
| Coliforms | |
| CFU per 100 mL | MMM 4.2W |

-continued

| Test | Method |
|---|---|
| Thermotolerant Coliforms | |
| CFU per 100 mL | MMM 4.3W |
| E. Coli | |
| CFU per 100 mL | MMM 4.3W |
| Pseudomonas Aeruginosa | |
| CFU per 100 mL | MMM 4.5W |

Heterotrophic Plate Count (HPC) is used as an indicator for general water quality. The test requires bacterial incubation at temperatures of 21° C. and 37° C. for a set time. Colonies of <100 CFU per mL are generally acceptable in swimming pools. The coliform group and particularly the thermotolerant coliform group (E. Coli) are considered serious from a human hygiene viewpoint. Nil colonies of coliforms are permitted in safe swimming pool water. The presence of pseudomonas aeruginosa in swimming pools is responsible for ear infection in swimmers. Nil colonies of P. aeruginosa are a requirement for safe swimming pool water.

TABLE 7

| | Test Results | | | |
|---|---|---|---|---|
| | Date 2 Nov. 2004 Treatment Duration | | | |
| | 0 minutes | 10 minutes | 15 minutes | 30 minutes |
| | Lab Number | | | |
| Sample Condition | 0428810W Untreated | 0428811W Treated | 0428812W Treated | 0428813W Treated |
| Heterotrophic Plate Count | | | | |
| at 21°C CFU per mL | 1,900 | 960 | 50 | 0 |
| at 37°C CFU per mL | 2,300 | 1,700 | 610 | 0 |
| Coliforms | | | | |
| CFU per 100 mL | 0 | 0 | 0 | 0 |
| Thermotolerant Coliforms | | | | |
| CFU per 100 mL | 0 | 0 | 0 | 0 |
| E. Coli | | | | |
| CFU per 100 mL | 0 | 0 | 0 | 0 |
| Pseudomonas Aeruginosa | | | | |
| CFU per 100 mL | 0 | 0 | 0 | 0 |

While microbial contamination in the swimming pool water was limited to Heterotrophic bacteria, the results demonstrate the efficacy of the method of the present invention to provide acceptable control over particular bacteria within a thirty minutes treatment period.

Advantageously, the inventors have provided a method for controllably releasing an anti-microbial agent into a fluid that is not directly reliant on an external electrical power source, such as is required for electrolytic techniques.

Numerous variations and modifications will suggest themselves to persons skilled in the relevant art, in addition to those already described, without departing from the basic inventive concepts. All such variations and modifications are to be considered within the scope of the present invention, the nature of which is to be determined from the foregoing description.

For example, the methods of the present invention are readily applicable to treatment of recirculating water and air used in evaporative air-conditioning systems. Evaporative air conditioners work on the principle of drawing in warm air and passing it through a series of wetted filter pads that cool it through evaporation before discharging the air into the space to be cooled. Evaporation of the water in the filter pad lowers the temperatures of the air and increases its humidity. An anti-microbial agent as described herein can be controllably released into recirculated water used in evaporative air-conditioning systems in accordance with the methods described herein in order to reduce the number of viable micro-organisms contained in the recirculated water. The treated recirculated water is circulated through, and wets, the series of filter pads in the system, where a proportion of the treated water is retained. The warm air passing through the wetted filter pads is humidified with the treated water, and micro-organisms contained in the warm air can also be subsequently reduced. Advantageously, the method of the present invention is not only readily able to treat the recirculated water with an anti-microbial agent but the warm air passing through the filter pads as well.

The claims defining the invention are as follows:

1. A method of controllably releasing an anti-microbial agent into a fluid comprising the steps of:
    contacting the fluid with a solid material comprising an anti-microbial agent containing one or more of silver oxide (AgO), copper (II) oxide, and zinc (II) oxide dispersed in a hydraulic cement binder in a ratio of between 50:50 to 95:5 wt % of the solid material;
    abrading an interface of the solid material and removing particles therefrom to expose an underlying surface of the solid material to the fluid,
    thereby facilitating release of the anti-microbial agent into the fluid from the underlying surface of the solid material and/or from the removed particles,
    wherein the step of abrading the interface of the solid material comprises providing at least one solid body not made of the solid material and agitating the fluid or otherwise causing the at least one solid body to collide on a controlled basis with the interface of the solid material,
    wherein the step of agitating the fluid comprises containing the fluid and the or each solid body in a vessel and recirculating the fluid through the vessel, such that the flux of fluid into or out of the vessel causes the or each solid body to collide with the solid material, and
    wherein an interior surface of the vessel is coated with the solid material.

2. A method of controllably releasing an anti-microbial agent into a fluid comprising the steps of:
    contacting the fluid with a solid material comprising an anti-microbial agent containing one or more of silver oxide (AgO), copper (II) oxide, and zinc (II) oxide dispersed in a hydraulic cement binder in a ratio of between 50:50 to 95:5 wt % of the solid material;
    abrading an interface of the solid material and removing particles therefrom to expose an underlying surface of the solid material to the fluid,
    thereby facilitating release of the anti-microbial agent into the fluid from the underlying surface of the solid material and/or from the removed particles,
    further comprising the step of forming an inert film or coating on the interface of the solid material.

3. The method according to claim 2, wherein the forming of the inert film or coating follows ceasing the abrading thereby allowing the inert film or coating to form on the interface of the solid material.

4. A system for controllably releasing an anti-microbial agent into a fluid, the system comprising:
- a receptacle for receiving the fluid;
- a solid material comprising an anti-microbial agent containing one or more of silver oxide (AgO), copper (II) oxide, and zinc (II) oxide dispersed in a hydraulic cement binder in a ratio of 50:50 to 95:5 wt % of the solid material, wherein an interface of the solid material is disposed in the receptacle and is in contact with the fluid received in the receptacle; and
- a means for abrading the interface of the solid material and removing particles therefrom and exposing an underlying surface of the solid material to the fluid,
- thereby facilitating release of the anti-microbial agent from the underlying surface of the solid material and/or from the removed particles into the fluid,
- wherein the means for abrading the interface of the solid material comprises
  - (a) a means for agitating the fluid received in the receptacle and causing the solid bodies to collide on a controlled basis thereby partially fragmenting the solid bodies and releasing the anti-microbial agent into the fluid, or
  - (b) a plurality of solid bodies not made of the solid material disposed in the receptacle and a means for agitating the fluid received in the receptacle and causing the solid bodies to collide on a controlled basis with the interface of the solid material,
- wherein the means for agitating the fluid is an impeller or stirring means.

5. A system for controllably releasing an anti-microbial agent into a fluid, the system comprising:
- a receptacle for receiving the fluid;
- a solid material comprising an anti-microbial agent containing one or more of silver oxide (AgO), copper (II) oxide, and zinc (II) oxide dispersed in a hydraulic cement binder in a ratio of 50:50 to 95:5 wt % of the solid material, wherein an interface of the solid material is disposed in the receptacle and is in contact with the fluid received in the receptacle; and
- a means for abrading the interface of the solid material and removing particles therefrom and exposing an underlying surface of the solid material to the fluid,
- thereby facilitating release of the anti-microbial agent from the underlying surface of the solid material and/or from the removed particles into the fluid,
- wherein the means for abrading the interface of the solid material comprises
  - (a) a means for agitating the fluid received in the receptacle and causing the solid bodies to collide on a controlled basis thereby partially fragmenting the solid bodies and releasing the anti-microbial agent into the fluid, or
  - (b) a plurality of solid bodies not made of the solid material disposed in the receptacle and a means for agitating the fluid received in the receptacle and causing the solid bodies to collide on a controlled basis with the interface of the solid material,
- wherein the means for agitating the fluid is a means for shaking the receptacle and its contents.

6. A method of treating a fluid with an anti-microbial agent comprising the steps of:
- contacting the fluid with a solid material comprising an anti-microbial agent containing one or more of silver oxide, copper (II) oxide, and zinc (II) oxide dispersed in a hydraulic cement binder in a ratio between 50:50 to 95:5 wt % of the solid material; and
- abrading an interface of the solid material and removing particles therefrom to expose an underlying surface of the solid material to the fluid, thereby facilitating release of the anti-microbial agent from the underlying surface of the solid material and/or from the removed particles into the fluid,
- wherein the step of abrading the interface of the solid material comprises providing at least one solid body not made of the solid material and agitating the fluid or otherwise causing the or each solid body to collide on a controlled basis with the interface of the solid material,
- wherein an interior surface of the vessel is coated with the solid material.

7. A method of treating a fluid with an anti-microbial agent comprising the steps of:
- contacting the fluid with a solid material comprising an anti-microbial agent containing one or more of silver oxide, copper (II) oxide, and zinc (II) oxide dispersed in a hydraulic cement binder in a ratio between 50:50 to 95:5 wt % of the solid material; and
- abrading an interface of the solid material and removing particles therefrom to expose an underlying surface of the solid material to the fluid, thereby facilitating release of the anti-microbial agent from the underlying surface of the solid material and/or from the removed particles into the fluid, and
- forming an inert film or coating on the surface of the solid material,
- wherein the step of abrading the interface of the solid material comprises providing a plurality of solid bodies of the solid material and agitating the fluid or otherwise causing the solid bodies to collide on a controlled basis and thereby partially fragment the solid bodies and release an effective amount of the anti-microbial agent into the fluid, and
- wherein the step of agitating the fluid comprises containing the fluid and the solid bodies in a vessel, and recirculating the fluid through the vessel, such that the flux of fluid into or out of the vessel causes the solid bodies to collide.

8. A method of treating a fluid with an anti-microbial agent comprising the steps of:
- contacting the fluid with a solid material comprising an anti-microbial agent containing one or more of silver oxide, copper (II) oxide, and zinc (II) oxide dispersed in a hydraulic cement binder in a ratio between 50:50 to 95:5 wt % of the solid material; and
- abrading an interface of the solid material and removing particles therefrom to expose an underlying surface of the solid material to the fluid, thereby facilitating release of the anti-microbial agent from the underlying surface of the solid material and/or from the removed particles into the fluid, and
- ceasing the step of abrading and allowing an inert film or coating to form on the interface of the solid material,
- wherein the step of abrading the interface of the solid material comprises providing a plurality of solid bodies of the solid material and agitating the fluid or otherwise causing the solid bodies to collide on a controlled basis and thereby partially fragment the solid bodies and release an effective amount of the anti-microbial agent into the fluid, and
- wherein the step of agitating the fluid comprises shaking the fluid at a rate which causes the solid bodies to collide.

* * * * *